(12) United States Patent
Schulz et al.

(10) Patent No.: US 8,747,821 B2
(45) Date of Patent: *Jun. 10, 2014

(54) TRANSPARENT COSMETIC OR DERMATOLOGICAL FORMULATION

(75) Inventors: Ulrike Schulz, Hamburg (DE); Gordon Christ, Frankfurt (DE)

(73) Assignee: Beiersdorf AG, Hamburg (DE)

( * ) Notice: Subject to any disclaimer, the term of this patent is extended or adjusted under 35 U.S.C. 154(b) by 1812 days.

This patent is subject to a terminal disclaimer.

(21) Appl. No.: 10/574,231

(22) PCT Filed: Mar. 10, 2005

(86) PCT No.: PCT/EP2005/051068
§ 371 (c)(1),
(2), (4) Date: Aug. 31, 2006

(87) PCT Pub. No.: WO2005/105026
PCT Pub. Date: Nov. 10, 2005

(65) Prior Publication Data
US 2008/0233066 A1    Sep. 25, 2008

(30) Foreign Application Priority Data

Apr. 27, 2004   (DE) .................. 10 2004 020 711

(51) Int. Cl.
*A61K 8/26* (2006.01)
*A61K 8/28* (2006.01)
*A61K 8/36* (2006.01)
*A61K 8/365* (2006.01)
*A61Q 15/00* (2006.01)

(52) U.S. Cl.
USPC ............... 424/65; 424/66; 424/68; 514/557; 514/570; 514/944

(58) Field of Classification Search
None
See application file for complete search history.

(56) References Cited

U.S. PATENT DOCUMENTS

| | | | |
|---|---|---|---|
| 3,509,253 A | 4/1970 | Babbin | |
| 3,991,176 A * | 11/1976 | Rubino | ............... 424/47 |
| 4,078,050 A | 3/1978 | Hart | |
| 4,921,694 A | 5/1990 | Hoppe et al. | |
| 5,318,778 A | 6/1994 | Schmucker et al. | |
| 5,571,841 A | 11/1996 | Yu et al. | |
| 5,587,153 A | 12/1996 | Angelone, Jr. et al. | |
| 5,648,067 A | 7/1997 | Dillenburg et al. | |
| 5,652,266 A | 7/1997 | Bobier-Rival et al. | |
| 5,677,339 A * | 10/1997 | Yu et al. | ............... 514/557 |
| 5,718,888 A | 2/1998 | Klier et al. | |
| 5,776,494 A * | 7/1998 | Guskey et al. | ............... 424/414 |
| 5,863,525 A | 1/1999 | Angelone, Jr. et al. | |
| 5,925,388 A | 7/1999 | Moineau et al. | |
| 6,042,816 A | 3/2000 | Shen | |
| 6,156,296 A | 12/2000 | Riedel et al. | |
| 6,468,551 B1 | 10/2002 | Diec et al. | |
| 6,585,983 B1 | 7/2003 | Gers-Barlag et al. | |
| 6,593,283 B2 * | 7/2003 | Hei et al. | ............... 510/214 |
| 6,911,210 B1 | 6/2005 | Bormann et al. | |
| 6,942,871 B2 | 9/2005 | Bruning et al. | |
| 7,189,406 B1 * | 3/2007 | Gross | ............... 424/401 |
| 2002/0077372 A1 | 6/2002 | Gers-Barlag et al. | |
| 2003/0059396 A1 * | 3/2003 | Bhakoo et al. | ............... 424/76.1 |
| 2003/0065027 A1 | 4/2003 | Brock et al. | |
| 2003/0175221 A1 | 9/2003 | Gers-Barlag et al. | |
| 2005/0265940 A1 | 12/2005 | Okada | |

FOREIGN PATENT DOCUMENTS

| | | |
|---|---|---|
| AU | 49509/93 | 3/1994 |
| DE | 3740186 | 1/1989 |
| DE | 3938140 | 8/1991 |
| DE | 4009347 | 9/1991 |
| DE | 4204321 | 8/1993 |
| DE | 4229707 | 3/1994 |
| DE | 4229737 | 3/1994 |
| DE | 4237081 | 5/1994 |
| DE | 4309372 | 9/1994 |
| DE | 4324219 | 1/1995 |
| DE | 69523805 | 10/1995 |
| DE | 4423450 | 1/1996 |
| DE | 19519404 | 11/1996 |
| DE | 19602111 | 7/1997 |
| DE | 19608775 | 9/1997 |
| DE | 19842787 | 3/2000 |
| DE | 19844261 | 3/2000 |
| DE | 19857235 | 6/2000 |
| DE | 19919481 | 11/2000 |
| DE | 10107628 | 8/2002 |
| EP | 0775486 | 5/1997 |
| GB | 1541396 | 2/1979 |
| GB | 2280111 | 1/1995 |
| GB | 2280111 A * | 1/1995 |
| WO | 92/05767 | 4/1992 |
| WO | 98/15255 | 4/1998 |
| WO | 98/32418 | 7/1998 |

OTHER PUBLICATIONS

Transparent. (2010). In Merriam-Webster Online Dictionary. Retrieved Jul. 15, 2010, from http://www.merriam-webster.com/dictionary/transparent.*
U.S. Appl. No. 10/574,219 entitled "Aqueous Anti-Perspiration Formulation", (2006).
U.S. Appl. No. 10/574,230 entitled "Transparent Cosmetic Microemulsion-Based Formulation Containing an Alph-Hydroxycarboxylic Acid", (2006).
U.S. Appl. No. 11/586,585 entitled "Optically Appealing Cosmetic or Dermatological Preparation", (2006).

\* cited by examiner

*Primary Examiner* — Brian-Yong Kwon
*Assistant Examiner* — Christopher R Lea
(74) *Attorney, Agent, or Firm* — Abel Law Group, LLP

(57) ABSTRACT

The invention relates to a clear, cosmetic and dermatological formulation having reduced stickiness, comprising at least one antiperspirant active ingredient and/or deodorant active ingredient, at least one α-hydroxycarboxylic acid and water.

24 Claims, No Drawings

TRANSPARENT COSMETIC OR DERMATOLOGICAL FORMULATION

CROSS-REFERENCE TO RELATED APPLICATIONS

The present application is a U.S. National stage of International Application No. PCT/EP2005/051068, filed Mar. 10, 2005, which claims priority of German Patent Application No. 10 2004 02 0711.9, filed Apr. 27, 2004.

BACKGROUND OF THE INVENTION

1. Field of the Invention

The invention relates to a clear, cosmetic and dermatological formulation with reduced stickiness.

2. Discussion of Background Information

For aesthetic reasons in particular, transparent and translucent products are preferred by many consumers. Thus, transparent formulations are often used, for example, as deodorant or antiperspirant (AP). These can nowadays be realized by the following technologies:
1. aqueous-alcoholic formulations
2. water-in-silicone emulsions
3. microemulsions The aqueous-alcoholic deodorant and AP formulations are mostly based on water and alcohol as medium, deodorant and antiperspirant agents as active ingredients, and also perfume, solubilizers and thickeners (mostly based on carbohydrate) as additional agents. They are perceived by the consumer as being fresh and cooling, but are at the same time encumbered with a whole series of disadvantages. Thus, for example, application primarily to freshly shaved skin is associated with incompatibilities as a result of the alcohol content. Another major disadvantage is the fact that relatively large amounts of oil cannot be incorporated into such systems. As a result of the high content of antiperspirant salt required for highly effective performance, a white residue remains following application to the skin; this is perceived by the consumer as being extremely troublesome. However, due to the absence of a sufficiently large oil phase for technical reasons, this cannot be concealed. Moreover, the use of carbohydrate thickeners leads to high stickiness of the product after the alcohol has evaporated.

Water-in-silicone emulsions belong to the group of water-in-oil emulsions. The water phase comprising ethanol or polyhydric alcohols, such as, for example, propylene glycol and water-soluble active ingredients, such as AP agent and/or deodorant active ingredient, constitutes about 75-90% of the formulation. The oil phase consists of a volatile and a non-volatile silicone oil and also a silicone emulsifier.

The transparency of water-in-silicone emulsions is based on matching the refractive indices of the two phases. It is a drawback that even a difference in the indices of 0.0004 caused, for example, by evaporation, leads to cloudiness. WO 98/32418 and WO 92/05767 describe such deodorant or AP formulations based on W/Si emulsion.

One approach for solving the described disadvantages has been made possible through cosmetically pleasing alcohol-free and transparent products which are based on so-called microemulsions. These have the major advantage that even relatively large amounts of various oils—with all of the described positive effects for the consumer—can be stably incorporated. Formulations of this type are in principle available by means of phase inversion temperature technology (PIT) or high-pressure homogenization. The required stability of the emulsifier system to high concentrations of antiperspirant salts, however, places high demands on the formulation skill of the product developer.

WO 98/15255 describes microemulsions. However, a drawback even with these formulations is a sticky feel on the skin caused by the thickener, and the lack of a yield point.

It is an object of the present invention to provide a cosmetic preparation which enriches the prior art and helps to avoid its disadvantages.

In particular, it is the object of the present invention to provide a cosmetic and/or dermatological formulation which is transparent and is characterized by minimized stickiness. In particular, the object was to provide a deodorant or antiperspirant formulation which is transparent and has no cloudiness at all, which is characterized by a minimized stickiness and which has a defined yield point for optimized discharge and application.

SUMMARY OF THE INVENTION

The present invention provides a transparent cosmetic and/or dermatological formulation comprising (a) one or more antiperspirant active ingredients and/or one or more deodorant active ingredients, (b) one or more α-hydroxycarboxylic acids and (c) water.

In one aspect of the formulation, component (b) may comprise mandelic acid.

In another aspect, component (a) may comprise at least one antiperspirant active ingredient. For example, component (a) may comprise at least one aluminum salt such as, e.g., aluminum chlorohydrate and/or one or more aluminum zirconium salts.

In yet another aspect of the formulation of the present invention, the ratio of antiperspirant active ingredient(s) to α-hydroxycarboxylic acid(s) may be from 15:1 to 1:1, e.g., from 12:1 to 2:1, or from 10:1 to 2.5:1.

In a still further aspect, the formulation may comprise the antiperspirant active ingredient(s) in an amount of from 1% to 35% by weight, e.g., from 1% to 25% by weight, or from 1% to 20% by weight, based on the total weight of the formulation.

In another aspect, the formulation may comprise component (b) in an amount of from 0.1% to 10% by weight, e.g., from 0.1% to 8% by weight, based on the total weight of the formulation.

In another aspect, the formulation may have a defined yield point and/or it may be in a form which is suitable for application to the human skin.

The present invention also provides a transparent cosmetic and/or dermatological antiperspirant formulation which comprises (a) an antiperspirant active ingredient which comprises at least one aluminum salt, (b) an α-hydroxycarboxylic acid which comprises mandelic acid and (c) water.

In one aspect, the formulation may comprise component (a) in an amount of from 1% to 35% by weight, e.g., in an amount of up to 25% by weight, and component (b) in an amount of from 0.1% to 10% by weight, e.g., in an amount of up to 8% by weight, each based on the total weight of the formulation.

In another aspect, the ratio of component (a) to component (b) may be from 10:1 to 2.5:1.

In yet another aspect of the formulation, component (a) may comprise aluminum chlorohydrate an/or one or more aluminum zirconium salts.

The present invention also provides a transparent cosmetic and/or dermatological antiperspirant formulation which is suitable for application to the human skin and comprises (a) from 1% to 20% by weight of one or more antiperspirant active ingredients which comprise aluminum chlorohydrate and/or one or more aluminum zirconium salts, (b) from 0.1% to 8% by weight of mandelic acid and (c) water.

In one aspect of the formulation, the ratio of component (a) to component (b) may be from 10:1 to 2.5:1. In another aspect, the formulation may have a defined yield point.

The present invention also provides a transparent antiperspirant and/or deodorant hydrogel which comprises a formulation according to the present invention, including the various aspects thereof as set forth above.

DETAILED DESCRIPTION OF THE INVENTION

It was surprising and unforeseeable by the person skilled in the art that a cosmetic formulation comprising at least one antiperspirant active ingredient, at least one α-hydroxycarboxylic acid and water gels to afford a transparent, viscous to pasty formulation and permits the provision of a transparent and low-stick cosmetic antiperspirant and/or deodorant preparation.

Through the surprisingly simple combination of antiperspirant active ingredients and at least one α-hydroxycarboxylic acid in water it is possible to prepare transparent cosmetic and dermatological formulations which have no objectively or subjectively perceived stickiness at all.

α-Hydroxycarboxylic acid is used to refer to organic acids which, besides the COOH group or groups, comprise one or more OH groups in the α position relative to one of the carboxyl functionalities. The hydroxy acids therefore have the properties of carboxylic acids and alcohols or phenols at the same time. The hydroxy acids include some natural substances, such as mandelic acid, lactic acid, malic acid, tartaric acid and other fruit acids. According to the invention, all hydroxy acids which can be used in cosmetics are hereby disclosed.

Besides enzymatic fermentation, which is used for a number of naturally occurring hydroxy acids (e.g. for lactic acid using Lactobacillus delbrueckii), the preparation of the hydroxy acids takes place, for example, by nucleophilic substitution of α-halocarboxylic acids with hydroxyl ions or from carbonyl compounds via cyanohydrins (see FIG. 1).

FIG. 1—Preparation of α-Hydroxy Acids

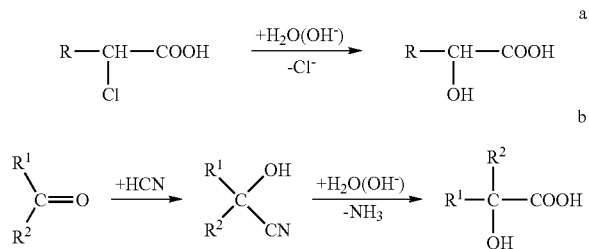

Particular preference is given to hydroxyphenylacetic acid or else phenylglycolic acid with the formula $H_5C_6$—CH(OH)—COOH, $C_8H_8O_3$, known under the name mandelic acid. Mandelic acid is readily soluble in water, alcohol, ether and 2-propanol. Synthetically, (±)-mandelic acid is obtained from benzaldehyde and hydrocyanic acid via the α-hydroxynitrile (cyanohydrin) and its acidic hydrolysis corresponding to FIG. 2:

FIG. 2: Preparation of Mandelic Acid

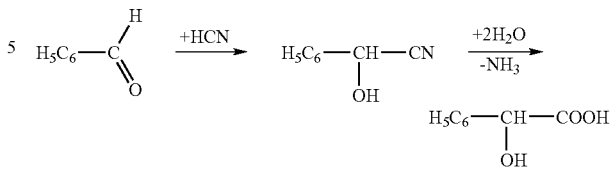

By means of the α-hydroxycarboxylic acids, in particular mandelic acid, it is surprisingly possible to prepare an AP and/or deodorant preparation which permits the required properties, such as transparency and low stickiness and, moreover, also the establishment of a specific yield point of the preparation. Furthermore, the formulation according to the invention is absorbed very rapidly into the skin without leaving residues behind.

The yield point is a term for the smallest shear stress above which a plastic material behaves in rheological terms like a liquid (DIN 1342-1: 1983-10). The yield point is determined by recording a flow curve (DIN 53019: 1980-05; DIN 53214: 1982-02). The value obtained is heavily dependent on the timescale (stress rate) on which the measurement is based. This is irrespective of whether the measurement is carried out using a shear stress-controlled or speed-controlled viscometer. Short timescales (rapid stresses) generally produce higher values for the yield point. An excessively high yield point may be the cause of flow disturbances. On the other hand, with a suitably dimensioned yield point it is possible to suppress the tendency of the liquid formulation to run.

The preparation according to the invention is therefore advantageously in the form of a gel or hydrogel and has a yield point, as a result of which placement and application is improved compared to preparations from the prior art.

The combination according to the invention of AP active ingredient, α-hydroxycarboxylic acid, in particular mandelic acid, and water allows the production of a transparent cosmetic preparation via a unique thickening mechanism. The user thus has for the first time a water-clear and nevertheless extremely effective preparation at his disposal. The preparation according to the invention is easy to apply in gel form and has a pleasant feel on the skin on account of the lack of stickiness.

As antiperspirant active ingredient it is advantageously possible to incorporate acidic aluminum salts and/or aluminum/zirconium salts in aqueous solution. Here, the concentration ranges described refer to the so-called active contents of the antiperspirant complexes: in the case of the aluminum compounds, to anhydrous complexes, in the case of the aluminum/zirconium compounds, to water- and buffer-free complexes. The buffer used here is usually glycine.

The list which follows of antiperspirant active ingredients which are to be used advantageously is in no way intended to be limiting:

aluminum salts (of the empirical formula $[Al_2(OH)_mCl_n]$, where m+n=6):
    aluminum chlorohydrate $[Al_2(OH)_5Cl] \times H_2O$
    standard Al complexes: Locron L, Locron LIC, Locron LIF (Clariant), Chlorhydrol
    (Reheis), ACH-303 (Summit), Aloxicoll L (Giulini)
    activated Al complexes: Reach 501 (Reheis), Aloxicoll 51L
    aluminum sesquichlorohydrate $[Al_2(OH)_{4.5}Cl_{1.5}] \times H_2O$
    standard Al complexes: Aloxicoll 31L (Giulini), Westchlor 186 (Westwood Chemicals)

activated Al complexes: Reach 301 (Reheis)
aluminum dichlorohydrate [$Al_2(OH)_4Cl_2$]×$H_2O$
aluminum-zirconium salts:
  aluminum/zirconium trichlorohydrex glycine [$Al_4Zr(OH)_{13}Cl_3$]×$H_2O$×Gly
  standard Al/Zr complexes: Rezal 33GC (Reheis), AZG-7164 (Summit)
  aluminum/zirconium tetrachlorohydrex glycine [$Al_4Zr(OH)_{12}Cl_4$]×$H_2O$×Gly
  standard Al/Zr complexes: Rezal 36, Rezal 36G, Rezal 36 GC (Reheis), AZG-368 (Summit), Zirkonal L435G (Giulini), Westchlor ZR 35 BX5, Westchlor ZR 41 (Westwood Chemicals)
  aluminum/zirconium pentachlorohydrex glycine [$Al_8Zr(OH)_{23}Cl_5$]×$H_2O$×Gly
  standard Al/Zr complexes: Rezal 67 (Reheis), Zirkonal L540, Zirkonal L530 PG (Giulini), Westchlor ZR 80B (Westwood Chemicals)
  aluminum/zirconium octachlorohydrex glycine [$Al_8Zr(OH)_{20}Cl_8$]×$H_2O$×Gly: Westchlor ZR 82B Glycine-free aluminum/zirconium salts can, however, also likewise be used advantageously.

The antiperspirant active ingredients are used in the formulations according to the invention in an amount of from 1 to 35% by weight, preferably from 1 to 20% by weight.

Deodorants can also advantageously be added to preparations according to the invention. Customary cosmetic deodorants are based on various activity principles.

By using antimicrobial substances in cosmetic deodorants it is possible to reduce the bacteria flora on the skin. Here, in the ideal case, only the odor-causing microorganisms should be effectively reduced. The flow of perspiration itself is not influenced as a result, in an ideal case only the microbial decomposition of the perspiration is stopped temporarily. The combination of astringents with antimicrobially effective substances in one and the same composition is also customary.

All active ingredients customary for deodorants can be used advantageously, for example odor concealers, such as customary perfume constituents, odor absorbers, for example the sheet silicates described in DE 40 09 347, of these in particular montmorillonite, kaolinite, illite, beidellite, nontronite, saponite, hectorite, bentonite, smectite, also, for example, zinc salts of ricinoleic acid. Antimicrobial agents are likewise suitable for incorporation into the preparations according to the invention. Advantageous substances are, for example, 2,4,4'-trichloro-2'-hydroxydiphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the active agents described in DE 37 40 186, DE 39 38 140, DE 42 04 321, DE 42 29 707, DE 42 29 737, DE 42 37 081, DE 43 09 372, DE 43 24 219. Sodium hydrogencarbonate can also be used advantageously.

The amount of deodorants (one or more compounds) in the preparations is preferably 0.01 to 10% by weight, preferably 0.05 to 5% by weight, based on the total weight of the preparation.

By means of the α-hydroxycarboxylic acids, in particular mandelic acid, and the AP active ingredient—aluminum salt—it is surprisingly possible to produce a hydrogel which has the required properties, such as transparency and low stickiness. Moreover, the formulation according to the invention is absorbed very rapidly into the skin without leaving residues behind. Table 1 shows the comparison of various transparent formulations in a sensory research panel consisting of 8 trained testers. For this, the samples were applied to the skin in a defined amount and evaluated by reference to an evaluation scale (1=not sticky; 10=considerably sticky).

TABLE 1

| | Example according to the invention Transparent hydrogel | Comparative examples | | |
|---|---|---|---|---|
| | | Nanoemulsion | Water-in-silicone emulsion | Aqueous-alcoholic formulation |
| Ability to soak in, in seconds | 95 | 179 | 153 | 106 |
| Stickiness scale from 1-10 | 3.4 | 5.2 | 6.5 | 5.3 |

A combination of mandelic acid and aluminum chlorohydrate where the ratio of aluminum chlorohydrate to mandelic acid is 15:1 to 1:1, preferably 12:1 to 2:1, in particular 10:1 to 2.5:1 has proven to be particularly advantageous.

The cosmetic and dermatological preparations according to the invention can comprise cosmetic auxiliaries as are customarily used in such preparations, e.g. preservatives, bactericides, UV filters, antioxidants, water-soluble vitamins, mineral substances, suspended solid particles, perfumes, substances for preventing foaming, dyes, pigments which have a colouring effect, thickeners, moisturizing and/or humectant substances or other customary constituents of a cosmetic or dermatological formulation, such as alcohols, polyols, polymers, foam stabilizers or silicone derivatives.

The transparent gel-like preparation according to the invention is advantageously prepared by dissolving the α-hydroxycarboxylic acids in water. The aqueous AP active ingredients, in particular aluminum salt solution, are then added with stirring.

To apply the preparation, conventional packagings for deodorants and/or antiperspirants can be used, e.g. stick dispensers, gel dispensers, tubes and roll-ons.

Data in percent by weight based on the total mass of the preparation.

| | Examples | | |
|---|---|---|---|
| | 1 | 2 | 3 |
| Aluminum chlorohydrate | 5 | 10 | 10 |
| Mandelic acid | 1.4 | 1.8 | 2 |
| Sodium citrate | — | — | 1 |
| Water | 93.6 | 88.2 | 87 |
| Total | 100 | 100 | 100 |

What is claimed is:

1. A cosmetic or dermatological formulation, wherein the formulation is transparent and comprises (a) at least one antiperspirant active ingredient, (b) mandelic acid and (c) water, (a), (b) and (c) being present in ratios which result in gelling.

2. The formulation of claim 1, wherein (a) comprises at least one aluminum salt.

3. The formulation of claim 2, wherein (a) comprises aluminum chlorohydrate.

4. The formulation of claim 1, wherein (a) comprises at least one aluminum zirconium salt.

5. The formulation of claim 1, wherein a ratio (a):(b) is from 15:1 to 1:1.

6. The formulation of claim 5, wherein the ratio is from 12:1 to 2:1.

7. The formulation of claim 5, wherein the ratio is from 10:1 to 2.5:1.

8. The formulation of claim 1, wherein the formulation comprises (a) in an amount of from 1% to 35% by weight, based on a total weight of the formulation.

9. The formulation of claim 8, wherein the formulation comprises (a) in an amount of from 1% to 25% by weight.

10. The formulation of claim 8, wherein the formulation comprises (a) in an amount of from 1% to 20% by weight.

11. The formulation of claim 1, wherein the formulation comprises (b) in an amount of from 0.1% to 10% by weight, based on a total weight of the formulation.

12. The formulation of claim 11, wherein the formulation comprises (b) in an amount of from 0.1% to 8% by weight.

13. The formulation of claim 1, wherein the formulation further comprises a deodorant active ingredient.

14. The formulation of claim 1, wherein the formulation has a defined yield point.

15. The formulation of claim 1, wherein the formulation is present as a hydrogel.

16. A cosmetic or dermatological antiperspirant formulation, wherein the formulation is free from zirconium containing antiperspirant active ingredients and transparent and comprises (a) an antiperspirant active ingredient which comprises one or more aluminum salts, (b) at least one α-hydroxycarboxylic acid and (c) water, (a), (b) and (c) being present in ratios which result in gelling.

17. The formulation of claim 16, wherein (a) comprises aluminum chlorohydrate.

18. The formulation of claim 16, wherein (a) consists of aluminum chlorohydrate.

19. The formulation of claim 16, wherein (b) comprises mandelic acid.

20. The formulation of claim 16, wherein the formulation comprises (a) in an amount of from 1% to 25% by weight and (b) in an amount of from 0.1% to 10% by weight, each based on a total weight of the formulation.

21. The formulation of claim 16, wherein a ratio (a):(b) is from 10:1 to 2.5:1.

22. A cosmetic or dermatological antiperspirant formulation, wherein the formulation is transparent and suitable for application to human skin and comprises (a) from 1% to 20% by weight of an antiperspirant active ingredient which comprises one or both of an aluminum salt and an aluminum zirconium salt, (b) from 0.1% to 8% by weight of mandelic acid and (c) water, (a), (b) and (c) being present in ratios which result in gelling.

23. The formulation of claim 22, wherein a ratio (a):(b) is from 10:1 to 2.5:1.

24. The formulation of claim 23, wherein the formulation has a defined yield point.

* * * * *